United States Patent [19]

McCarty

[11] Patent Number: 5,647,837

[45] Date of Patent: Jul. 15, 1997

[54] TUMESCENCE SUSTAINING APPLICATOR

[76] Inventor: Donald L. McCarty, P.O. Box 1558, Julian, Calif. 92036

[21] Appl. No.: 413,842

[22] Filed: Mar. 30, 1995

[51] Int. Cl.$^6$ ............................................. A61F 5/41
[52] U.S. Cl. .......................................................... 600/38
[58] Field of Search ........................... 600/38–41; 601/6, 601/11, 12; 128/842, 844

[56] References Cited

U.S. PATENT DOCUMENTS

| | | | |
|---|---|---|---|
| 4,753,227 | 6/1988 | Yanuck, Jr. | 600/41 |
| 5,020,522 | 6/1991 | Stewart | 600/38 |
| 5,125,890 | 6/1992 | Merrill et al. | 600/39 |
| 5,234,401 | 8/1993 | Yamanaka | 600/38 |

FOREIGN PATENT DOCUMENTS

| | | | |
|---|---|---|---|
| 347300 | 8/1960 | Switzerland | 600/38 |

*Primary Examiner*—Lee S. Cohen
*Assistant Examiner*—Samuel Gilbert
*Attorney, Agent, or Firm*—Donald L. McCarty

[57] ABSTRACT

A non-invasive tumescence enhancing and sustaining applicator replaces or augments an existing applicator which is prescribed for use by men who have had surgery resulting in impotence, or circulation problems making it difficult or impossible to achieve an erection. Tumescence is achieved by applying a vacuum to the flaccid penis with an evacuated cylinder, there being an annular seal inside the cylinder which creates a sliding hermetic seal with the penis to permit the vacuum to be drawn and sustained even while the cylinder may be moving or moved axially relative to the penis.

7 Claims, 2 Drawing Sheets

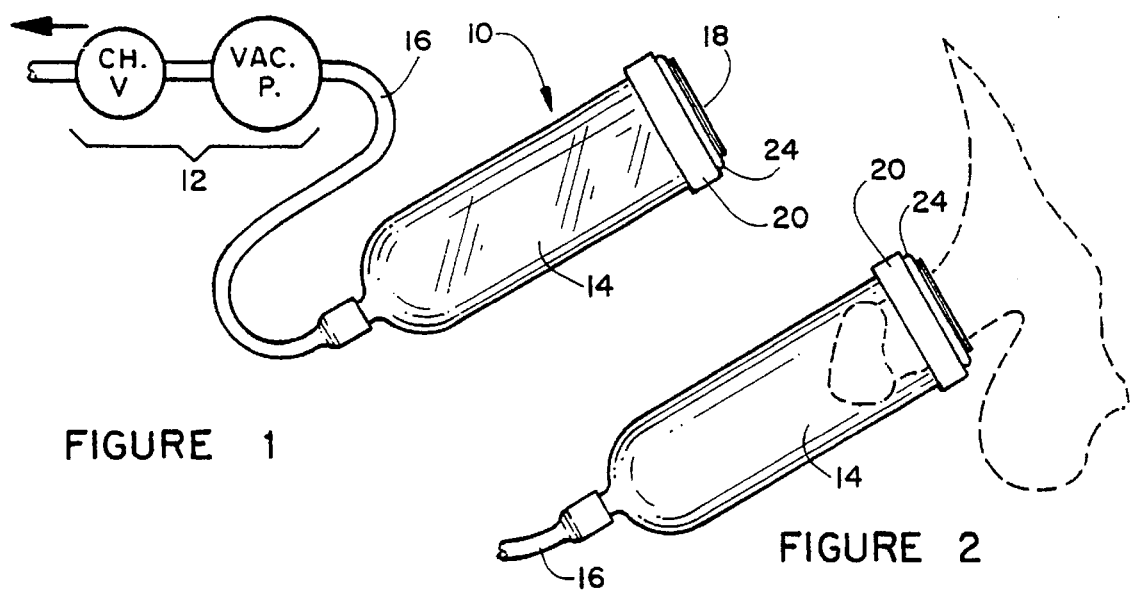
FIGURE 1
FIGURE 2
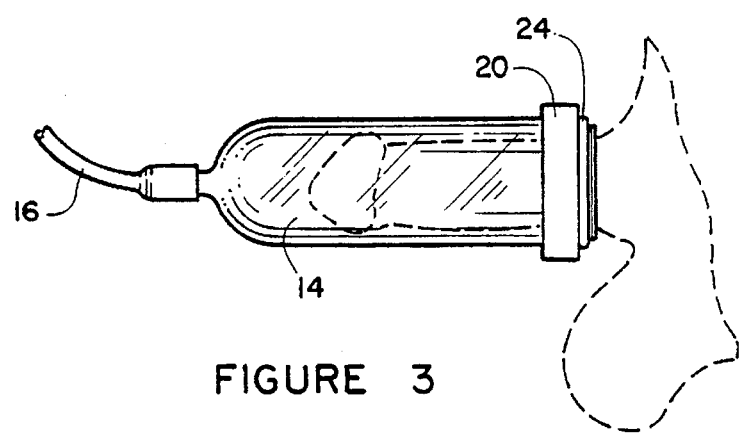
FIGURE 3
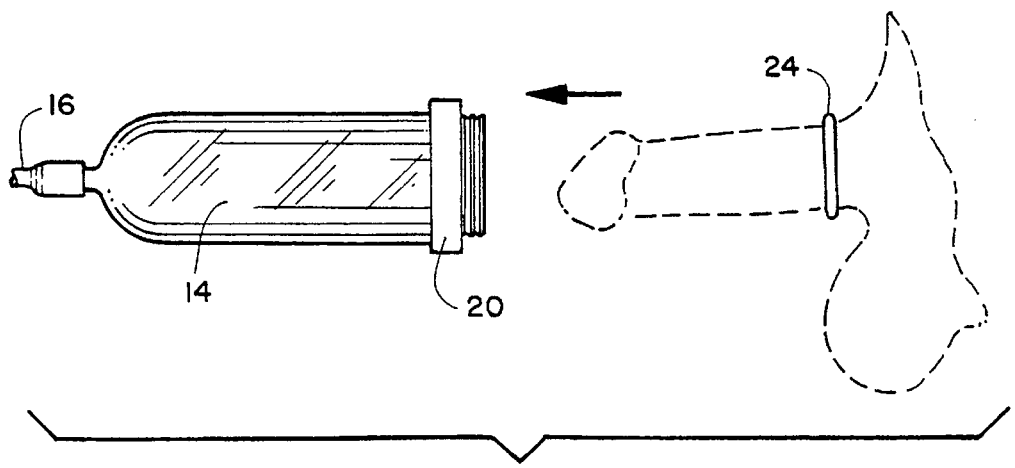
FIGURE 4

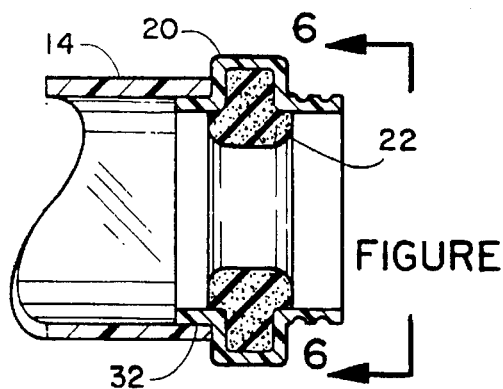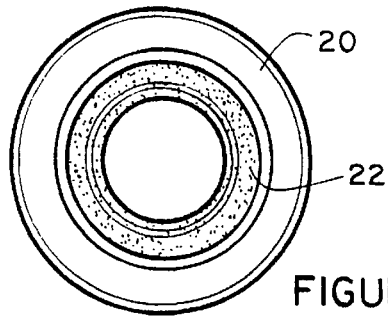
FIGURE 5
FIGURE 6
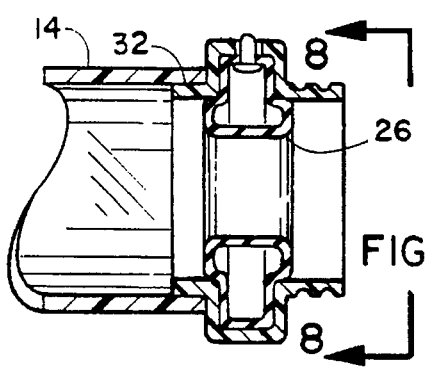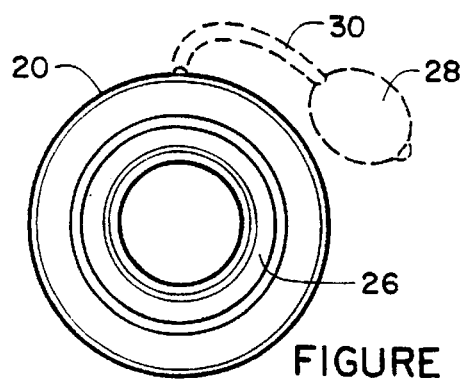
FIGURE 7
FIGURE 8
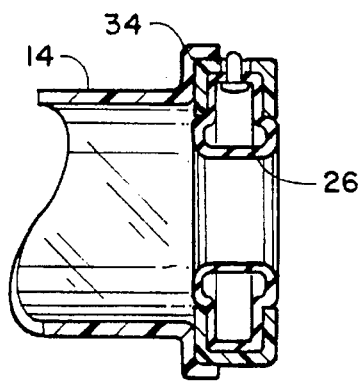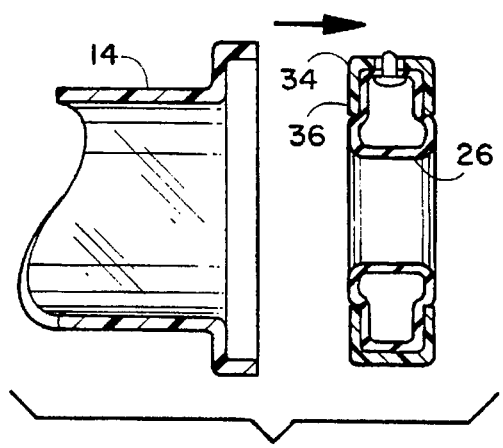
FIGURE 9
FIGURE 10

TUMESCENCE SUSTAINING APPLICATOR

BACKGROUND OF THE INVENTION

1. Field of the Invention

Many men, and especially older men, have had radical prostate surgery as a result of cancer of the prostate, or have circulation problems caused by aging, medication that they must take regularly, or debilitating disease, which makes it very difficult for them to accumulate the amount of blood necessary to engorge the penis to form an erection. In many cases there is not adequate blood circulation left in the penis to achieve even a partial erection.

2. Prior Art

For these persons, a device has been developed that is prescribed by physicians which is made of a hollow cylinder connected through a tube to a hand-held vacuum pump which evacuates the cylinder as it presses up against the groin. The vacuum created around the penis is sufficient to pull the blood in to engorge the penis, creating a satisfactory erection. In order to sustain the erection, a constrictor ring encircles the cylinder adjacent the open end which is the end of the cylinder which seals against the groin. When the cylinder is removed, the restrictor ring is snapped off of the cylinder and onto the penis where it acts as a tourniquet, retaining all of the blood that has been drawn into the penis.

3. Deficiencies in the Art

This apparatus is partially successful, at least with some men. However, it has serious design flaws that make it incapable of being completely successful with everyone, and incapable of being used at all with certain male candidates.

Many problems are caused by the fact that the instrument seals against the groin. First, the groin must be shaved or the seal cannot be made. After the vacuum has been drawn, the constrictor ring is on the outside of the cylinder adjacent the groin, so the cylinder must be pulled back from the groin to enable the ring to be snapped into place on the base of the penis. In addition to the virtually unavoidable sting of the snapping ring, as the open end of the cylinder pulls away from the groin, it tends to pull the scrotum inside. The ring can then snap onto the scrotum creating considerable discomfort and possibly defeating the desired effects of the erection as well.

This problem is at least greatly aggravated, if not caused outright, by the fact that the user must operate very quickly or the purpose will be defeated. The moment the cylinder is removed from the groin, the vacuum vents, and instantly the blood begins exiting the penis. By the time the restrictor ring is in place, half of the blood or more may be gone and the erection is defeated. Unless the patient is fast, the exercise will only bring frustration, and for some patients it will not work at all.

Patients falling into this category as well as others may have the tendency to operate the vacuum pump at excessive vacuum levels in order to over-engorge the penis to provide a margin for loss through drainage during the ring engaging step. This is not good for the patient. The higher pressure may damage blood vessels and cause problems associated with tissue edema.

Because the strong rubber-type rubber ring that is used with this device must snap into place fast and vigorously, it can hurt considerably.

There is a need for a device which achieves the purposes of the described apparatus, but does not cause a significant proportion of the vacuum to vent and the blood to drain during the tourniquet step, so that adequate erections can be attained and maintained. Such a device should allow the patient sufficient time to apply the restraint ring slowly and in a suitable position without losing the vacuum in the process, such that the tourniquet step would not be painful. With sufficient time to apply the restraint, there should not be an incentive to the patient to over-evacuate to compensate for blood loss, with the possibility of ensuing tissue and blood vessel damage.

SUMMARY OF THE INVENTION

The instant invention resolves problems caused by the deficiencies in the prior art with a vacuum-operated apparatus that works on the same effective principle as the prior art, that is, applying a vacuum to the penis and once it is engorged capturing the blood with a tourniquet-type restraint to prevent it from draining back when the vacuum is vented. The process is executed in a manner that is more effective than that of the solely groin-sealed embodiment presently in use. This improvement is achieved by sealing not against the groin, with the inherent tendency to inhale part of the scrotum, but rather with a sliding seal inside the cylinder which seals against the penis itself. The groin no longer requires close shaving, and once sealed, the cylinder may be actually moved on the penis without releasing the vacuum, enabling the ring to be properly positioned with ample time to work while applying and maintaining full vacuum. This not only solves the premature drainage problem, but also reduces the pain inasmuch as functionality does not depend on achieving a threshold ring snapping speed. The patient may position the ring on the most suitable place on the penis, such that a different position can be chosen for each application. This rotation is important for patients who are trying to avoid repeated stress on certain areas of tissue or blood vessels. Since the vacuum is being sustained while the constrictor ring is deployed, eliminating the need to hurry, there is no need for overevacuation, and no more snapping the scrotum painfully with the restrictor in the rush to control and maintain the erection.

In a refined embodiment of the invention, the sliding seal on the inside of the vacuum cylinder which enables the vacuum to be drawn doubles as a constrictor ring, and is removable from the vacuum cylinder so that it can take this role. In order to increase the compression of this annular element so that it can act as a tourniquet to prevent blood flow right after use as a seal permitting blood to flow out into the penis, it is made inflatable, and is controlled by a sphygmomanometer-type bulb or similar inflation device, which is independent from the vacuum creating pump used for the main cylinder. The apparatus of the invention is much more comfortable for the patient and greatly reduces the risk of trauma to the vessels and tissue of the penis since no elastic type restriction device is required to maintain the blood volume.

BRIEF DESCRIPTION OF THE DRAWINGS

FIG. 1 is a side view of the invention;

FIG. 2 illustrates the use of the invention on a flaccid penis;

FIG. 3 illustrates that step in the sequence of using the invention in which the penis is engorged with the vacuum still applied;

FIG. 4 illustrates the end result with the constrictor ring around the base of the penis and the cylinder removed;

FIG. 5 is a longitudinal section taken through the invention at the point of the annular seal;

FIG. 6 is a section taken along Line 6—6 of FIG. 5;

FIG. 7 is a view similar to that of FIG. 5 but showing an inflated seal;

FIG. 8 is a section taken along Line 8—8 of FIG. 7;

FIG. 9 is a section similar to that of FIGS. 5 and 7 but of an embodiment in which the annular seal is removable to become the restrictor ring, the ring being inflatable and pressure-adjustable pressure using the hand or electric pump; and FIG. 10 is a section taken along Line 10—10 of FIG. 9.

DETAILED DESCRIPTION OF THE PREFERRED EMBODIMENTS

The invention is shown in its entirety at 10 in FIG. 1, and the sequence of the steps involved in it use are shown in FIGS. 2, 3 and 4 showing, respectively, initial application of the cylinder, evacuation of the cylinder, and the engagement of the constrictor ring around the penis near the base at the groin. The apparatus of FIGS. 2 through 4 also closely resembles the prior art device, except that the latter is pressed up tightly against the groin while the vacuum is being drawn and does not provide the luxury of permitting a space between itself and the groin as does applicant's device as illustrated. However, some patients, depending on their anatomy, may wish to initially start up against the groin with the device to enlarge the penis to seat against the inner seal of the invention as detailed below.

A small hand-operated or electric pump with a built-in check valve is indicated diagrammatically at 12. This pump is effective to create an adequate vacuum in the cylinder 14, which is transparent so that the operator can monitor progress. The cylinder 14 is sealed at the outer end of the tube 16 so the only possible place for the vacuum to escape would be from the open end 18. To seal at this end, an annular seal 20 is built into the base of the cylinder and is yielding enough, being made of resilient foam 22, that used with a thick lubricant it will seal against the penis to enable the vacuum to be drawn, but it will not seal so tightly as to interrupt blood flow. Some patients may find that it is preferable for the cylinder to seal primarily against the groin initially, until a vacuum is created to start the engorgement of the penis, so that it swells enough that the annular seal is effective.

The cylinder shown in FIG. 5 is used in conjunction with a constrictor ring 24 shown in FIG. 3 on the outside of the open end of the cylinder. The sliding lubricated seal 22 will seal at substantially any position along the length of the penis, and enables the cylinder to be pulled out slightly while the restrictor ring 24 is nudged off of the cylinder and into place near the base of the penis at a position chosen by the patient. A double ring is shown in FIGS. 5 through 8, which is recommended by some doctors for some patients.

Once the restraining ring is in place, the function of the vacuum is complete and the cylinder can be pulled off the penis. Use of the device is now finished.

Rather than achieving the sealing effect with a lubricated foam ring, the annular seal may be made to adjust dimensionally by being an inflatable bladder, as shown at 26 in FIGS. 7–10. With this embodiment, a pressure device 28 is connected to the annular ring through the tube 30. This pneumatic pump is independent from the vacuum pump used to create the cylinder vacuum so that independent control may be achieved. This is necessary as the amount of pressure required to seal the vacuum is very close to the amount of pressure that acts as a tourniquet to restrict blood flow. This embodiment allows the fine adjustments that may be required by the patient.

In the embodiments of both FIGS. 5 and 7, the cylinder and the annular seal could be provided as discrete pieces that separate from one another, with the cylinder resting on the ring housing 32, in sealing relationship therewith when in use. However it is not intended that these parts separate inasmuch as both parts have to be removed after the evacuation anyway.

In the third embodiment shown in FIGS. 9 and 10, however, it is mandatory that the cylinder be removed, and the cylinder itself defines an expanded radial plane that serves as a shoulder that butts up against the mating surface 36 of the annular bladder housing 34 of the constrictor ring. The greater the vacuum, the greater the force compressing this butt joint together. The bladder housing 34 is rigid, or at least form-retaining so it can support the annular bladder 26 which represents the inflatable portion of the ring. This unit is substantially the same type of seal housing as ring 32 but without the cylindrical extensions on both sides. It differs in function because the ring housing 34 of the embodiment of FIG. 9 is designed to separate from the cylinder 14 and remain on the penis, to be used as the constrictor ring as well as the sliding seal. There is no need to snap off a rubber band at all with this embodiment as the annular seal simply frees itself from the cylinder when the vacuum is released, after being pumped up to elevate the pressure from a sealing pressure to a pressure that applies a tourniquet effect, and remains on the penis as the constrictor ring to maintain the erection.

In any of the embodiments, the invention is a decided improvement over the prior art, and despite any deficiencies in the prior art, it has been a blessing to millions of men who were otherwise be substantially without remedy. The invention takes the concept of the prior art marketed product and removes the painful and ineffective aspects of it which may have been necessary in order to have the device accepted in the health professions, and replaces it with a medical apparatus which will seriously perform its prescribed duty without pain and uncertainty, and reduces the likelihood of tissue damage and frustration.

It is hereby claimed:

1. A tumescence sustaining applicator for an elongated compressible generally cylindrical two-state member having a hydraulically controlled tumescent state in which it is filled with fluid through internal ducts, and a flaccid state of diameter reduced from that of said tumescent state in which it is substantially drained of fluid, said applicator comprising:

(a) a vacuum cylinder which is gas impervious except at one open end and is connectable to a vacuum source;

(b) said cylinder having an internal annular seal adjacent said open end for establishing a substantially hermetic sliding seal around said elongated generally cylindrical two-state member when said member is inserted therein, said annular seal being substantially fixed against axial deformation and axial motion relative to said cylinder such that said seal moves axially with said cylinder substantially without deformation as said cylinder is moved axially along said member when said member is in said tumescent state, such that said seal can be slidingly adjusted axially relative to said member while sustaining a vacuum on said member to enhance the ability of said member to achieve said tumescent state;

(c) an elastic vasoconstrictor ring releasibly carried by said cylinder and having a constricted diameter adapted to be smaller than that of said elongated member in said tumescent state such that said ring is adapted to be released from said cylinder to engage around and compress said member to restrict the egress of fluid through said ducts and thereby prevent said member from entering said flaccid state when said vacuum is removed therefrom;

(d) wherein said seal and ring are combined as a unitary sealing ring, acting as a seal while drawing a vacuum from said source and becoming a restrictor ring when said vacuum cylinder is removed;

(e) wherein, said vacuum cylinder is freely axially adjustable on said member when in said tumescent state and said ring is releasible from said vacuum cylinder while said cylinder is applying a vacuum, at any axially related position thereon.

2. A tumescent sustaining applicator according to claim 1 wherein said sealing ring is inflatable and the applicator further including a means to pressurize said sealing ring.

3. A tumescent sustaining applicator according to claim 2 wherein said means to pressurize comprises an inflation bulb operatively connected to said inflatable sealing ring such that said bulb is operable with one hand to pressurize said ring.

4. A tumescent sustaining applicator according to claim 3 wherein said cylinder has releasible engagement means for engaging said ring and separates from said ring in use.

5. A tumescent sustaining applicator according to claim 4 wherein said releasible engagement means comprises an annular outwardly flared shoulder to butt up against said ring and increase the seal therewith as the vacuum in said cylinder is increased, causing ambient air to force said cylinder and ring ever more tightly together.

6. A method of sustaining tumescence in an elongated compressible generally cylindrical two-state member having a hydraulically controlled tumescent state in which it is filled with fluid through internal ducts, and a flaccid state in which it is substantially drained of fluid, and having a distal end, and a proximal end connected to a fluid supply through said ducts, by using a cylindrical vacuum cylinder which is gas impervious except at one open end and is connectable to a vacuum source, said cylinder having an internal annular seal wherein said annular seal is inflatable with means to inflate said seal, adjacent said open end for establishing a substantially hermetic sliding seal around said elongated generally cylindrical two-state member when same is inserted therein, such that said seal can be slidingly adjusted axially relative to said member while sustaining a vacuum on said member to enhance the ability of said member to achieve said tumescent state, and a a vasoconstrictor ring releasibly carried by said cylinder and having a constricted diameter smaller than that of said elongated member such that said ring can be released from said cylinder to engage around and compress said member to restrict the egress of fluid through said ducts and thereby prevent said member from entering said flaccid state when said vacuum is removed therefrom, said method comprising the following steps:

(a) connecting said cylinder to vacuum source;

(b) a engaging said cylinder over said member so that the distal end thereof projects through said open end of said cylinder and into said cylinder until said open end is near said proximal end and said member passes sealingly through said annular seal;

(c) applying a vacuum from said vacuum source until a partial vacuum is formed within said cylinder on the distal side of said annular seal adequate to effect tumescence in said member;

(d) sliding said cylinder axially along said member to expose a portion thereof where it is desired to engage said vasoconstricting ring on said member, and disengaging said ring from said cylinder and engaging same on said member;

(e) including a step executed as needed through out steps (b), (c), and (d), the step comprising inflating said seal with said means to inflate to a pressure level at which it substantially seals against said member, but stopping short of inflating said seal until said ducts are compressed stopping fluid circulation, and adjusting the inflation from time to time if necessary to maintain said pressure level; and (f) with said ring in place on said member, removing said cylinder.

7. A method according to claim 6 wherein said inflatable annular seal is separable from said cylinder, and step (d) includes the substep after sliding said cylinder to expose a portion of said member, of inflating said annular seal until it cuts off fluid circulation in said member and thereby becomes said constricting member, and then finishing step (d) by separating said ring from said cylinder.

* * * * *